(12) United States Patent
Masuda

(10) Patent No.: US 6,418,573 B1
(45) Date of Patent: Jul. 16, 2002

(54) BATHING METHOD AND BATHING APPARATUS

(76) Inventor: Masatoshi Masuda, 36, 100 banchi, Kitanokuchi, Mozume-cho, Mukou-shi, Kyoto-fu (JP)

( * ) Notice: Subject to any disclaimer, the term of this patent is extended or adjusted under 35 U.S.C. 154(b) by 0 days.

(21) Appl. No.: 09/634,746

(22) Filed: Aug. 9, 2000

(30) Foreign Application Priority Data

Aug. 12, 1999 (JP) ............................................. 11-228526
Aug. 23, 1999 (JP) ............................................. 11-234845

(51) Int. Cl.[7] ................................................. A61H 33/00
(52) U.S. Cl. ................................. 4/538; 4/525; 4/567
(58) Field of Search ............................ 4/538, 567, 568, 4/525, 524, 528, 529, 601–604; 5/606, 928

(56) References Cited

U.S. PATENT DOCUMENTS

| | | | | |
|---|---|---|---|---|
| 2,300,455 A | * | 11/1942 | Lukats | ............................ 4/525 |
| 3,653,376 A | | 4/1972 | Martin | |
| 4,055,863 A | * | 11/1977 | Duval | ............................ 4/567 |
| 4,130,120 A | | 12/1978 | Kohler, Jr. | |
| 4,307,714 A | * | 12/1981 | Weideman | ...................... 4/525 |
| 4,925,495 A | | 5/1990 | Crisp et al. | |
| 5,136,735 A | * | 8/1992 | Zimmerman | .................... 4/601 |
| 5,228,150 A | | 7/1993 | Parker | |
| 5,255,399 A | * | 10/1993 | Park | ............................. 4/525 |
| 5,441,529 A | * | 8/1995 | Dorsch | ........................... 4/568 |
| 5,664,593 A | * | 9/1997 | McClain | ......................... 4/603 |
| 5,839,135 A | * | 11/1998 | Kitamura | ....................... 4/601 |

FOREIGN PATENT DOCUMENTS

| | | | | |
|---|---|---|---|---|
| DE | 87 07 220 U | | 5/1988 | |
| FR | 2673837 B1 | * | 9/1992 | ..................... 4/525 |
| FR | 0 681 823 | | 11/1995 | |
| JP | 4-141168 B1 | * | 5/1992 | ..................... 4/524 |
| JP | 5-317197 B1 | * | 12/1993 | ..................... 4/601 |
| JP | 6-23009 B1 | * | 2/1994 | ..................... 4/601 |

* cited by examiner

*Primary Examiner*—Charles R. Eloshway
(74) *Attorney, Agent, or Firm*—Knobbe, Martens, Olson and Bear LLP.

(57) ABSTRACT

An apparatus includes a base having an opening on the top; a body supporting member having a number of openings, placed inside of the base; a lid covering the opening of the base; a plurality of upper shower nozzles arranged on the lid; a plurality of lower shower nozzles arranged under the body supporting member in the base; a hot-water supplying part; a hot-water supply route to connect a plurality of the upper shower nozzles and a plurality of the lower shower nozzles and the hot-water supplying part; and a heater to heat a space formed by the base and the lid.

17 Claims, 9 Drawing Sheets

BATHING METHOD AND BATHING APPARATUS

SUMMARY OF THE INVENTION

1. Field of the Invention

The present invention relates to bathing methods and bathing apparatus to automatically bathe a human body, and specifically to bathing methods and bathing apparatus which can be appropriately used for a cosmetic purpose.

2. Description of the Related Art

Conventional bathing apparatus are primarily used to bathe people who need care. In such bathing apparatus, a subject to be bathed remains lying on a stretcher during bathing. For example, Japanese Patent Laid-open No. 6-23009 discloses a shower bath apparatus having a structure in which shower water is flushed from above and below onto a subject to be bathed lying on a stretcher.

Summary of the Invention

However, the abovementioned conventional bathing apparatus are primarily to bathe people who need care and solely for a cleansing purpose. Therefore, conventional bathing apparatus cannot provide a subject to be bathed with cosmetic treatment or a health effect by relaxation or the like.

An objective of the present invention is to solve the abovementioned problem by providing a bathing method and a bathing apparatus which can improve the beauty and health of a subject to be bathed.

An embodiment of the invention is an apparatus comprising a base having an opening on the top; a body supporting member having a number of openings, placed inside of the base; a lid covering the opening of the base; a plurality of upper shower nozzles arranged on the lid; a plurality of lower shower nozzles arranged under the body supporting member in the base; a hot-water supplying part; a hot-water supply route to connect a plurality of the upper shower nozzles and a plurality of the lower shower nozzles and the hot-water supplying part; and a heating means to heat a space formed by the base and the lid. According to the embodiment of the present invention, a subject to be bathed can be provided with not only an effective cleansing but also a cosmetic treatment and a health effect by relaxation or the like. Thereby, the beauty and health of the subject to be bathed can be improved.

The present invention includes various embodiments as follows:

An embodiment of the invention is an apparatus wherein the heating means includes a far-infrared emission system to radiate far-infrared rays in a space formed by the base and the lid.

Another embodiment of the invention is an apparatus wherein the heating means includes a warm-air supply system having a warm-air generation part, a warm air ejection part to eject hot air into a space formed by the base and the lid, and a warm-air supply route to connect the warm-air ejection part and the warm-air generation part.

Another embodiment of the invention is an apparatus further comprising a steam supply system to mix steam with warm air passing through the warm-air supply route.

Another embodiment of the invention is an apparatus further comprising a cleansing agent reservoir to store a cleansing agent to cleanse a human body and a cleansing agent supplying means to mix the cleansing agent, stored in the cleansing agent reservoir, with hot-water passing through said hot-water supply route.

Another embodiment of the invention is an apparatus further comprising a lotion reservoir to store lotion, spray nozzles to eject like a mist the lotion stored in the lotion reservoir onto a space formed by the base and the lid, and a lotion supply route to connect the spray nozzles and the lotion reservoir.

Another embodiment of the invention is an apparatus further comprising a water-soluble-pack reservoir to store a water-soluble pack, and a water-soluble-pack supply route to connect the spray nozzles and the water-soluble-pack reservoir, spray nozzles to eject, like a mist, the water-soluble pack stored in said water-soluble pack reservoir onto a space formed by said base and said lid.

Another embodiment of the invention is an apparatus wherein the spray nozzles comprises a plurality of upper spray nozzles arranged on the lid and a plurality of lower spray nozzles arranged under the body supporting member in the base.

Additionally an embodiment of the invention is a bathing apparatus further comprising a swinging means to swing the upper shower nozzles and the lower shower nozzles.

Another embodiment of the invention is an apparatus further comprising a swinging means to swing the spray nozzles.

The present invention further includes an embodiment which is a method comprising a placement step to place a human body in a main apparatus consisting of a base having an opening on the top and a lid covering the opening of the base; a cleansing step to supply hot water and a cleansing agent to a human body in the main apparatus; a rinsing step to supply a hot water to a human body in the main apparatus.

Another embodiment of the invention is a method further comprising a drying step to supply warm air to a human body in the main apparatus, after the rinsing step.

Another embodiment of the invention is a method further comprising a lotion supplying step to supply lotion to a human body in the main apparatus, between the rinsing step and the drying step.

Another embodiment of the invention is a method further comprising a water-soluble-pack supplying step to supply a water-soluble pack to a human body in the main apparatus, between the cleansing step and the heating step and/or between the heating step and the rinsing step.

Another embodiment of the invention is a method wherein steam is admixed with the warm air in the heating step and/or the drying step.

Additionally, another embodiment of the invention is an apparatus comprising a main apparatus consisting of a base having an opening on the top and a body supporting member inside and a lid covering the opening of the base; a hot water supplying means to supply hot water to a human body in the main apparatus; a cleansing agent supplying means to supply a cleansing agent to a human body in the main apparatus; and a far-infrared supplying means to radiate far-infrared rays onto a human body in the main apparatus.

Another embodiment of the invention is an apparatus further comprising a means to supply lotion to a human body in the main apparatus.

Another embodiment of the invention is an apparatus further comprising a means to supply a water-soluble pack to a human body in the main apparatus.

Another embodiment of the invention is an apparatus further comprising a means to admix steam with warm air supplied by the means to supply warm air.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DETAILED DESCRIPTION OF THE PREFERRED EMBODIMENTS

Figure 1:
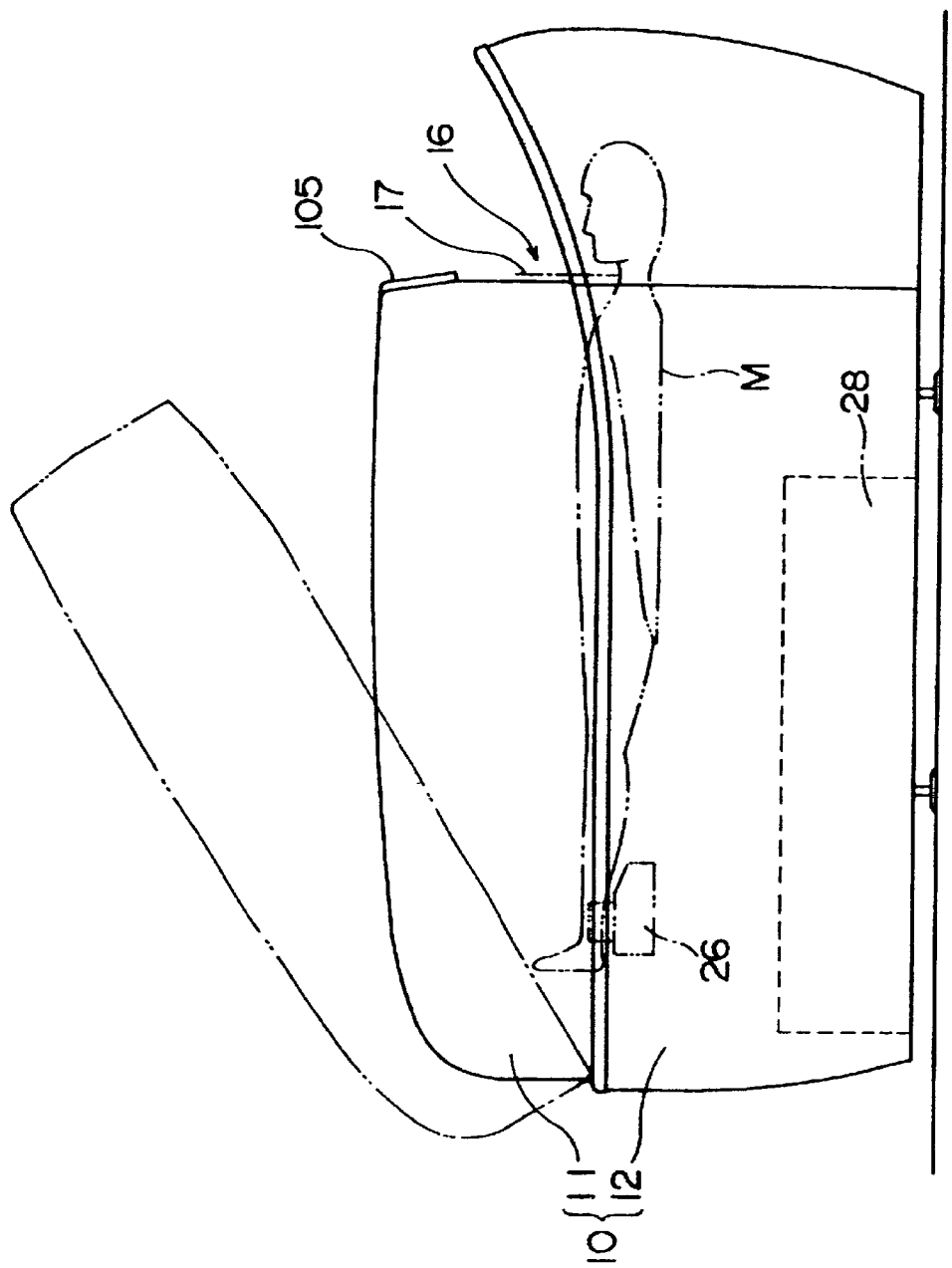
FIG. 1 is a general side view of the bathing apparatus according to the present invention.
Figure 2:
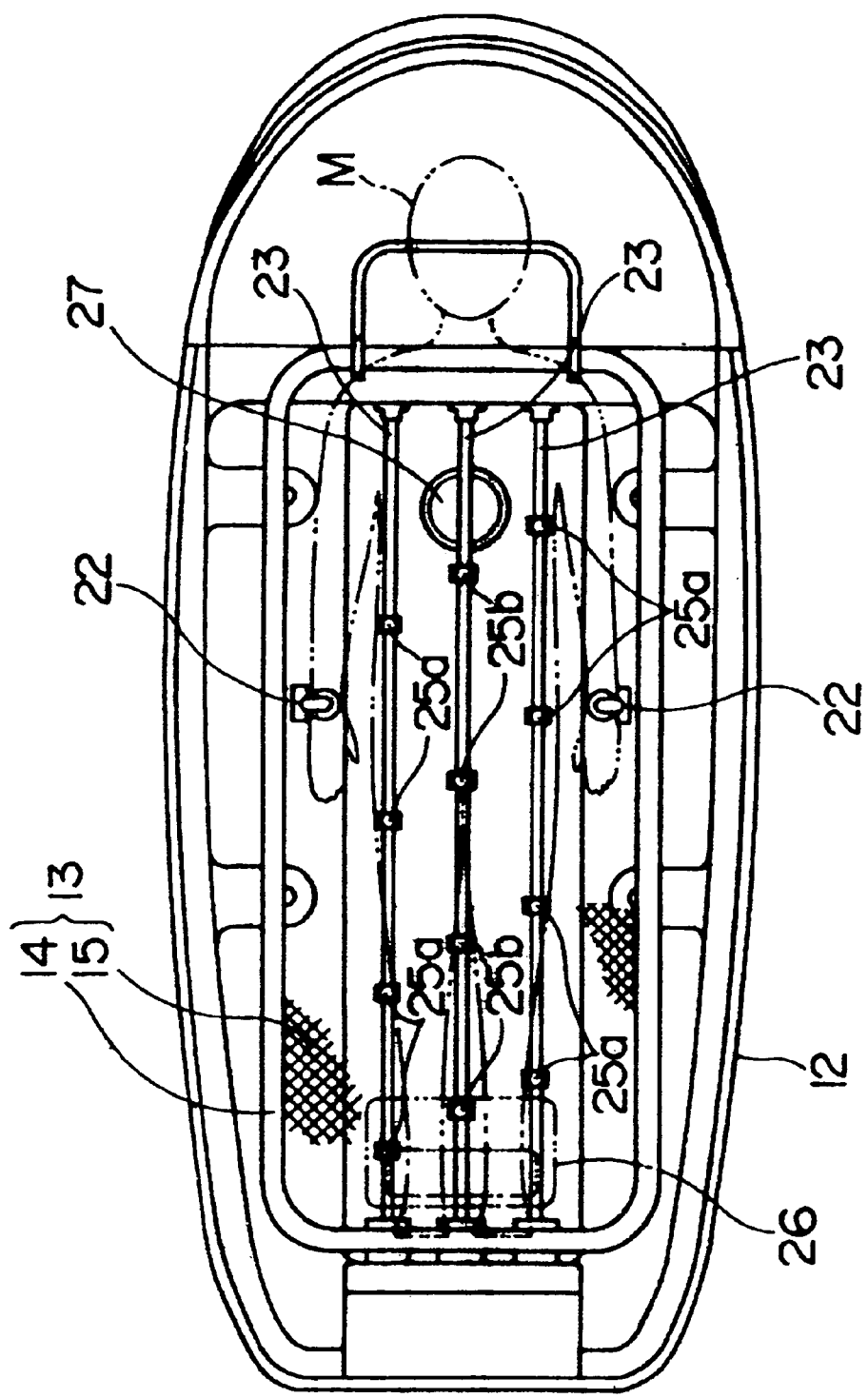
FIG. 2 is a top view of the bathing apparatus according to the present invention without the lid 11.
Figure 3:
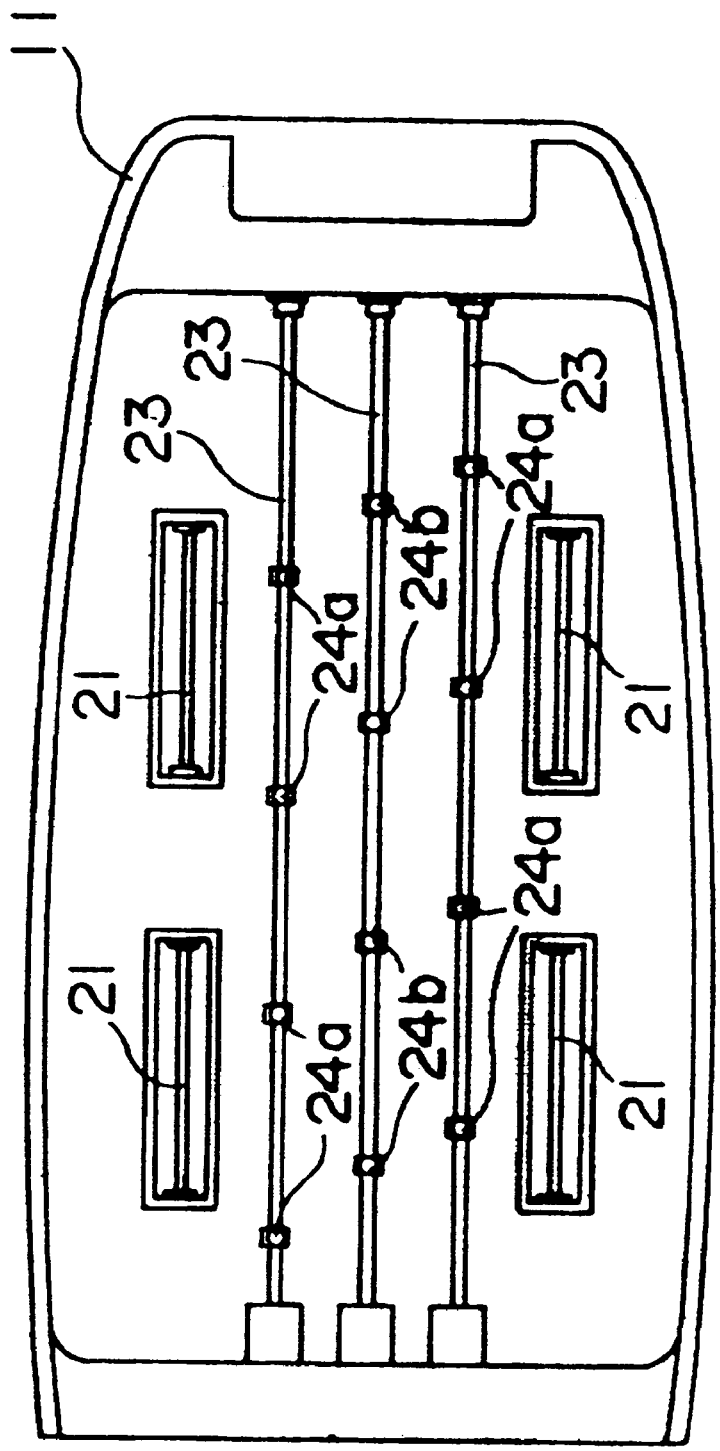
FIG. 3 is a bottom view of the lid 11, i.e., a view of its back side.

Embodiments of the present invention are now explained in detail referring to the drawings. FIG. 1 is a general side view of a bathing apparatus of the present invention. FIG. 2 is a top view of the apparatus without a lid 11. FIG. 3 is a bottom view of the lid 11, i.e., a view of its back side.

This bathing apparatus comprises a main apparatus 10 which consists of a base 12 having an opening on the top and a lid 11 covering the opening of the base 12. A subject to be bathed M is placed in the main apparatus 10. The lid 11 and the base 12 are made of molded resin. The lid 11 is hinged to the base 12.

The base 12 is equipped with a supporting member 13 to support a subject to be bathed. This supporting member 13 comprises a frame 14 and a netlike member 15 bound to this frame 14. Numerous openings to pass hot water or the like described hereinafter are formed on this netlike member 15.

The lid 11 is configured to cover most of the upper opening of the base 12. Further, the lid 11 has a waterproof curtain 17 which can be hung in front of an opening 16 formed on the opposite side of the hinge to the base 12.

In the bathing apparatus configured as described above, the subject to be bathed M enters or exits the main apparatus 10 when the lid 11 is open as shown with the double-dotted broken line in FIG. 1. The subject to be bathed M enters the main apparatus 10 and lies on the supporting member 13, then the lid 11 is closed as shown with the solid line in FIG. 1 such that only the head of the subject to be bathed M is exposed to external air while the trunk remains inside of the main apparatus 10.

On the bottom side of the lid 11, a plurality of far-infrared emission lamps 21 are mounted to radiate far-infrared rays onto the subject to be bathed M lying on the supporting member 13. A pair of right and left warm air ejection parts 22 to eject warm air mixed with steam into the main apparatus 10 are mounted under the supporting member 13 of the base 12. Further, a waste water recovering tank 28 to temporarily recover waste water is mounted at the bottom of the base 12.

Three shafts 23 which can each turn around its axial center are located on the lid 11. Four upper nozzles 24 are mounted on each shaft 23. Three shafts 23 which can each turn around its axial center are also located under the supporting member 13 of the base 12 and four lower nozzles 25 are mounted on each shaft 23. These shafts 23 are turned around individual axial center by a shaft driving mechanism. The upper nozzles 24 and the lower nozzles 25 swing with the turning of the shafts 23.

Figure 4:
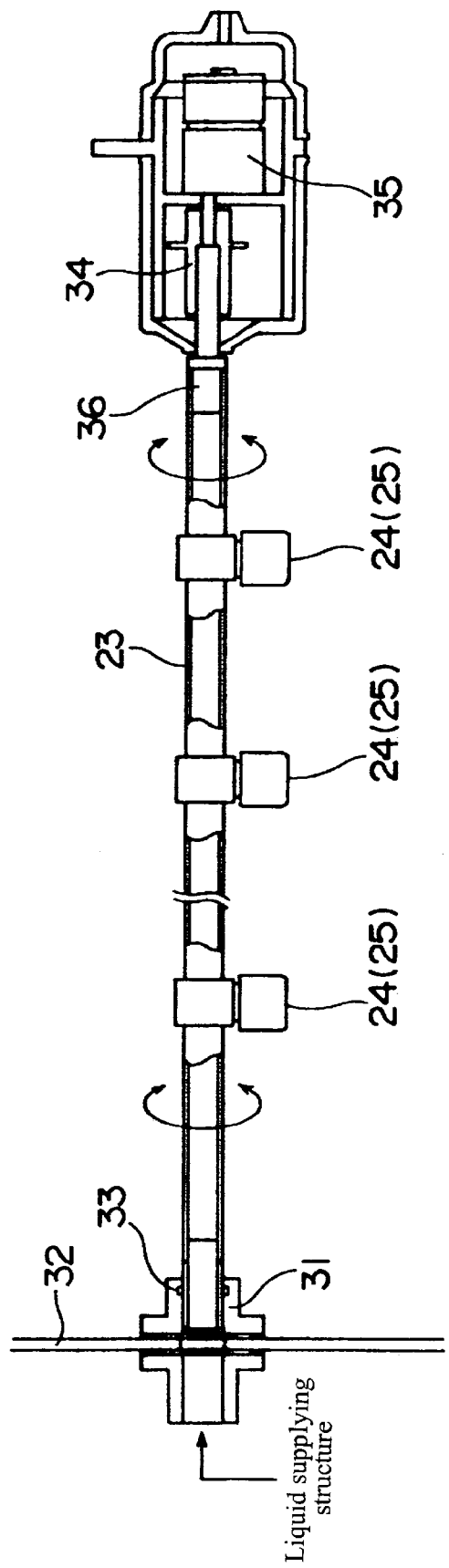
FIG. 4 is a cross section view showing the shaft driving mechanism to drive the shafts 23.

FIG. 4 is a cross section view of the shaft driving mechanism to turn these shafts 23.

One end of the shaft 23 pivots via a bearing 31 on the side wall 32 of the lid 11 or base 12. An O-ring 33 is placed between the shaft 32 and the bearing 31, to form an airtight connection between the outer perimeter of the shaft 23 and the inner perimeter of the bearing 31. The other end of the shaft 23 is connected, via a coupling 34, to a motor 35 mounted on the main apparatus. Thereby, the shaft 23 turns synchronously with the upper nozzles 24 (or lower nozzles 25) placed on it.

These shafts 23 are set in the head-to-leg direction of the supine subject to be bathed M (parallel with the lying subject to be bathed M). Accordingly, as the abovementioned shafts 23 turn, the upper nozzles 24 (or lower nozzles 25) swing in a left-and-right motion (up-and-down direction in FIGS. 2 and 3).

As shown in FIG. 4, the abovementioned shafts 23 are cylindrical. One end of the shaft 23 is connected to a liquid supply system 41, described hereinafter, to supply hot water or the like to the upper nozzles 24 (or the lower nozzles 25). The other end of the shaft 23 is plugged by a stopper 36.

In the abovementioned structure, hot water or the like supplied to the liquid supply system 41, described hereinafter, runs through the shafts 23 and is ejected, like a shower, from the upper nozzles 24 (or lower nozzles 25) toward the subject to be bathed M. Thus, the hot water or the like is supplied to the entire body of the subject to be bathed M with the swinging motion of the upper nozzles 24 (or lower nozzles 25).

Figure 5:
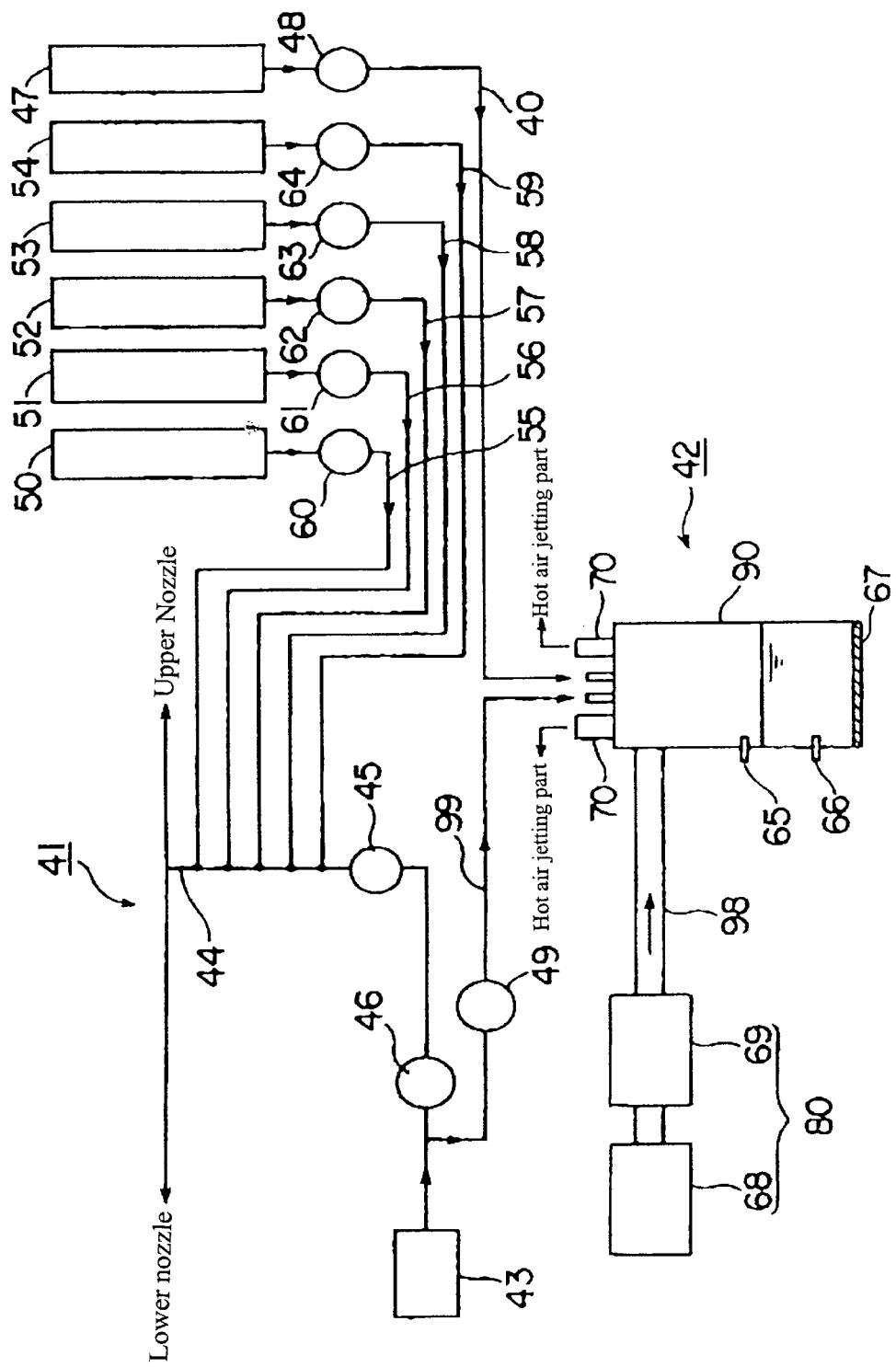
FIG. 5 is a block diagram showing the liquid supply system 41 and the steam/warm air supply system 42.

Next, the structures of the liquid supply system 41 to supply hot water or the like to the abovementioned upper nozzles 24 and lower nozzles 25 and a steam/warm air supply system 42 to supply warm air mixed with steam to the warm air ejection parts 22 will be explained. FIG. 5 is a block diagram of the liquid supply system 41 and the steam/warm air supply system 42.

The liquid supply system 41 has a hot-water supply route 44 to supply hot water stored in a hot-water storage tank 43, described in detail hereinafter, to the upper nozzles 24 and the lower nozzles 25. A solenoid valve 46 and a shower pump 45 are placed in this hot-water supply route 44. By operating the shower pump 45 while the solenoid valve 46 is opened, hot water stored in the hot-water storage tank 43 is moved to the upper nozzles 24 and the lower nozzles 25 and ejected from these upper nozzles 24 and lower nozzles 25 onto the subject to be bathed M in the main apparatus 10.

Further, the liquid supply system 41 has a cleansing agent reservoir 50 to store a cleansing agent to clean inside the main apparatus 10, a disinfectant reservoir 51 to store a disinfectant to disinfect inside the main apparatus 10, a body soap reservoir 52 to store a body soap to cleanse the human body, a lotion reservoir 53 to store lotion and a seaweed-pack reservoir 54 to store a seaweed pack as a water-soluble pack.

The abovementioned cleansing agent reservoir 50 is connected to the hot-water supply route 44 via a cleansing-agent supply route 55. A tube pump 60 to move a small amount of cleansing agent is placed inside the cleansing-agent supply route 55. Thus, by operating the tube pump 60, the cleansing agent stored in the cleansing agent reservoir 50 is moved toward the hot-water supply route 44 and a desired amount of the cleansing agent is admixed with hot water and thus can be supplied to the upper nozzles 24 and the lower nozzles 25.

Similarly, the abovementioned disinfectant reservoir 51 is connected to the hot-water supply route 44 via a disinfectant supply route 56. A tube pump 61 to move a small amount of disinfectant is placed inside the disinfectant supply route 56. Thus, by operating the tube pump 61, the disinfectant stored in the disinfectant reservoir 51 is moved toward the hot-water supply route 44 and a desired amount of the disinfectant is admixed with hot water and thus can be supplied to the upper nozzles 24 and the lower nozzles 25.

Similarly, the abovementioned body soap reservoir 52 is connected to the hot-water supply route 44 via a body-soap supply route 57. A tube pump 62 to move a small amount of body soap is placed inside the body-soap supply route 57. Thus, by operating the tube pump 62, the body soap stored in the body soap reservoir 52 is moved toward the hot-water supply route 44 and a desired amount of the body soap is admixed with hot water and thus can be supplied to the upper nozzles 24 and the lower nozzles 25.

Similarly, the abovementioned lotion reservoir 53 is connected to the hot-water supply route 44 via a lotion supply route 58. Inside the lotion supply route 58, a tube pump 63 to move a small amount of lotion is placed. Thus, by operating the tube pump 63, the lotion stored in the lotion reservoir 53 is moved toward the hot-water supply route 44 and a desired amount of the lotion is admixed with hot water and thus can be supplied to the upper nozzles 24 and the lower nozzles 25.

Similarly, the abovementioned seaweed-pack reservoir 54 is connected to the hot-water supply route 44 via a seaweed-pack supply route 59. A tube pump 64 to move a small amount of seaweed pack is placed inside the seaweed-pack supply route 59. Thus, by operating the tube pump 64, the seaweed pack stored in the seaweed-pack reservoir 54 is moved toward the hot-water supply route 44 and a desired amount of the seaweed pack is admixed with hot water and thus can be supplied to the upper nozzles 24 and the lower nozzles 25.

In the abovementioned embodiment, lotion and a seaweed pack are admixed with hot water to supply them to the body. However, when higher concentrations of lotion or a seaweed pack are required, the lotion or seaweed pack can be directly supplied to the upper nozzles 24 and the lower nozzles 25 from the lotion reservoir 53 or the seaweed-pack reservoir 54. In this case, special nozzles can be used instead of the upper nozzles 24 and the lower nozzles 25.

A steam/warm air supply system 42 has a warm air generation part 80, consisting of a ventilator 68 and a heater 69, and a steam generation part 90 connected to this warm air generation part 80 via a ventilating route 98.

A heater 67 is built in at the bottom of the abovementioned steam generation part 90. A pair of upper and lower water level sensors 65, 66 are mounted on the side wall of the steam generation part 90. Further, ventilating pipes 70 connected to a pair of warm air ejection parts 22 placed on the base 12 are located on the top of the steam generation part 90.

The steam generation part 90 is connected to the abovementioned hot-water storage tank 43 via a supply route 99. Thus, hot water stored in the hot-water storage tank 43 can be moved to the steam generation part 90 by operating the tube pump 49.

Hot water so moved is then stored in the steam generation part 90. The level of hot water is monitored and controlled by the pair of upper and lower water level sensors 65, 66. Hot water stored in the steam generation part 90 is then heated by the heater 67 to generate steam. This steam is mixed with warm air generated by the warm air generation part 80 and supplied via the ventilating pipe 70 to the pair of warm air ejection parts 22 placed inside the base 12.

Further, the steam/warm air generating system 42 has an aroma reservoir 47 to store an extract of aromatic herbs such as aroma oil used in aromatherapy (referred to as "aroma" in this specification). This aroma reservoir 47 is connected to the steam generation part 90 via an aroma supply route 40. A tube pump 48 to move a small amount of aroma is located in the aroma supply route 40. Thus, aroma stored in the aroma reservoir 47 can be moved to the steam generation part 90 by operating the tube pump 48.

Aroma moved from the aroma reservoir 47 to the steam generation part 90 is added dropwise into hot water stored in the steam generation part 90. The aroma is vaporized with the hot water using the heater 67. The vaporized aroma is admixed with warm air generated by the warm air generation part 80 and supplied via the ventilating pipes 70 to a pair of warm air ejection parts 22 placed inside the base 12.

Figure 6:
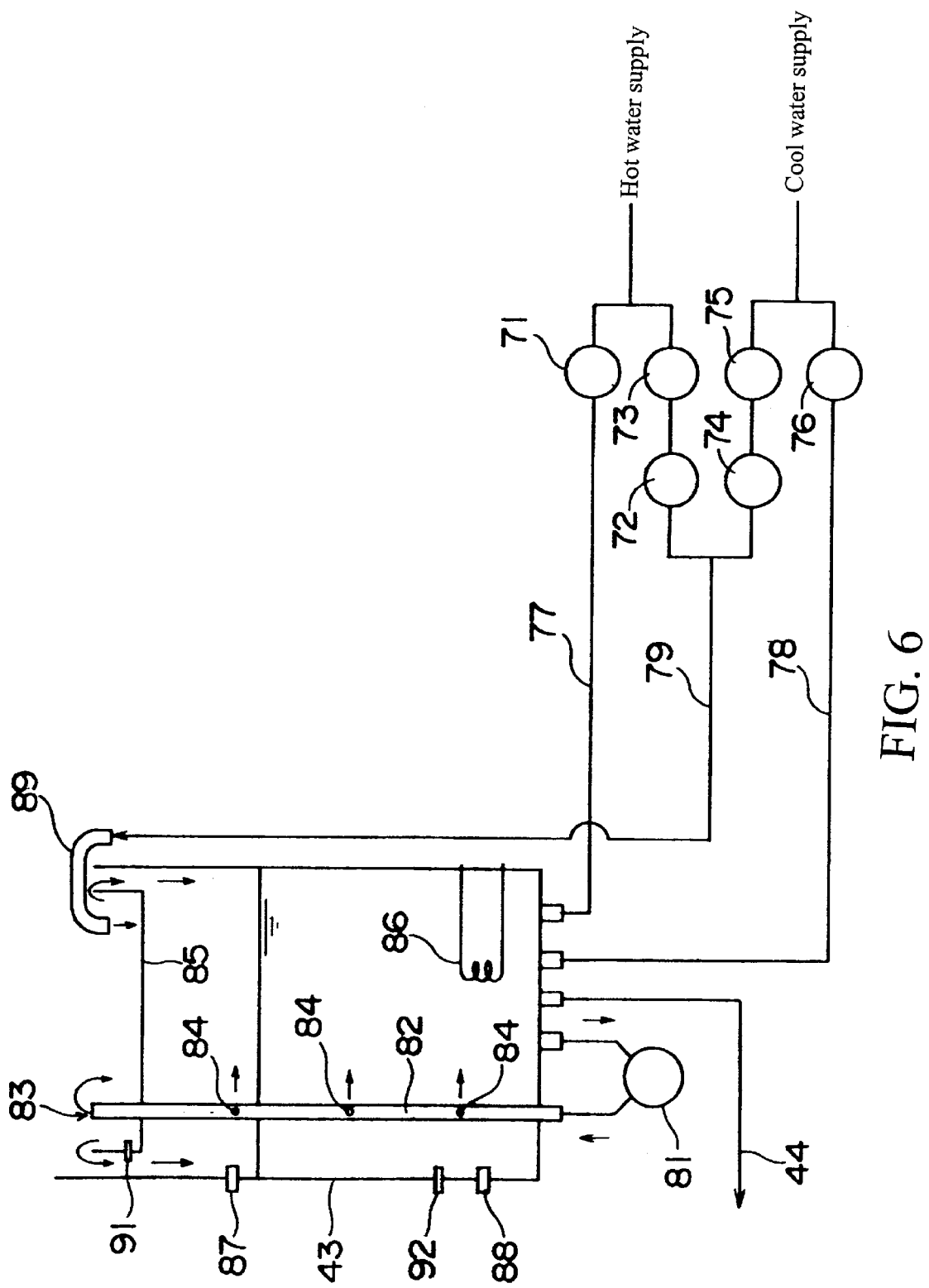
FIG. 6 is a block diagram showing the hot-water storage tank 43 along with the hot water and water supply system.

Next, the structure of the hot-water storage tank 43 which functions as a hot water supplying part in the liquid supply system 41 will be explained. FIG. 6 is a block diagram of the hot-water storage tank 43 along with a hot water and water supply system.

This hot-water storage tank 43 is to store hot water at a specified temperature. This hot-water storage tank 43 is connected via a pipe 77 to a hot-water supply source to supply hot water. A switching valve 71 is set in this pipe 77. Further, this hot-water storage tank 43 is connected via a pipe 78 to a water supply source to supply water at a normal temperature (tap water). A switching valve 76 is placed in this pipe 78.

Further, this hot-water storage tank 43 is also connected to a hot-water supply source and a water supply source via a pipe 79. A mixing valve mechanism consisting of a pair of flow control valves 72, 74 and a pair of switching valves 73, 74 are placed between the pipe 79 and the hot-water supply source and the water supply source. The pair of flow rate control valves 72, 74 can control the degree of opening based on the temperature of hot water detected by a temperature sensor 91 described hereinafter. Thus, hot water at an approximately constant temperature can be supplied in the pipe 79.

The hot-water storage tank 43 is equipped with a circulation pump 81 and a circulation pipe 82 to circulate hot water stored in the hot-water storage tank 43 and the temporary store tray 85 located in the upper part. Hot water stored in the hot-water storage tank 43 is sucked from the bottom by operating the circulation pump 81 into the circulation pipe 82. Then, a part of the hot water flows out from a plurality of the openings 84 formed on the circulation pipe 82 and the remaining part flows into the temporary store tray 85. The hot water flowing into the temporary store tray 85 overflows from the top and then runs down into the hot-water storage tank 43.

A temperature sensor 91 to measure the temperature of the hot water in the temporary store tray 85 is mounted on the side wall of the temporary store tray 85. A temperature sensor 92 to measure the temperature of the hot water in the hot-water storage tank 43 is equipped on the side wall of the hot-water storage tank 43. Further, a pair of upper and lower water level sensors 87, 88 to monitor the level of hot water in the hot-water storage tank 43 and a heater 86 to heat hot water in the hot-water storage tank 43 are mounted on the side wall of the hot-water storage tank 43.

Next, operation to store hot water in the hot-water storage tank 43 will be explained.

To start the storage of hot water in the hot-water storage tank 43, hot water from the hot-water supply source or normal temperature water from the water source is supplied to the hot-water storage tank 43 by opening the switching valves 71 and 76 while keeping the switching valves 73 and 75 closed. When the water level sensor 87 detects hot water, the switching valves 71 and 76 close. In this state, the hot water in the hot-water storage tank 43 is circulated by the circulation pump 81 and is heated by the heater 86. The temperature of the hot water in the hot-water storage tank 43 is detected by the temperature sensor 92. The temperature of the hot water in the hot-water storage tank 43 is kept constant by controlling the heater 86 based on the detected value.

In this state, if a decrease in hot water level caused by use of hot water in the hot-water storage tank 43 by the above-mentioned liquid supply system 41 is detected by the water level sensor 88, the switching valves 73 and 75 are opened, wherein hot water from the hot-water supply source and normal-temperature water from the water supply source are mixed together and supplied to the temporary store tray 85 via a U-shaped pipe 89. The extent to which the pair of flow rate control valves 72, 74 is opened is controlled by the temperature of the hot water in the temporary store tray 85 detected by the temperature sensor 91. Thus, hot water at a constant temperature is supplied to the temporary store tray 85 by the mixing valve mechanism.

Figure 7:
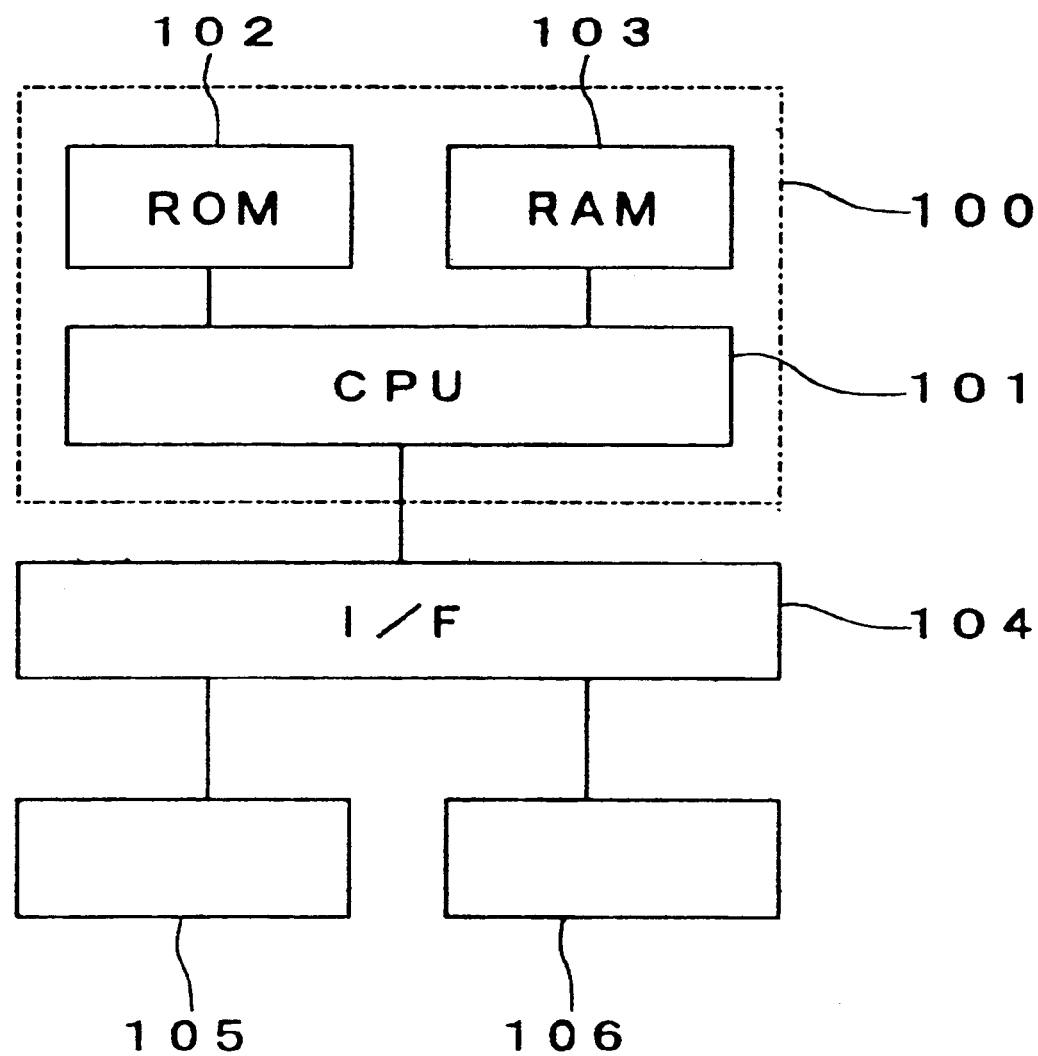
FIG. 7 is a block diagram showing the main electrical configuration of the bathing apparatus of the present invention.
Figure 8:
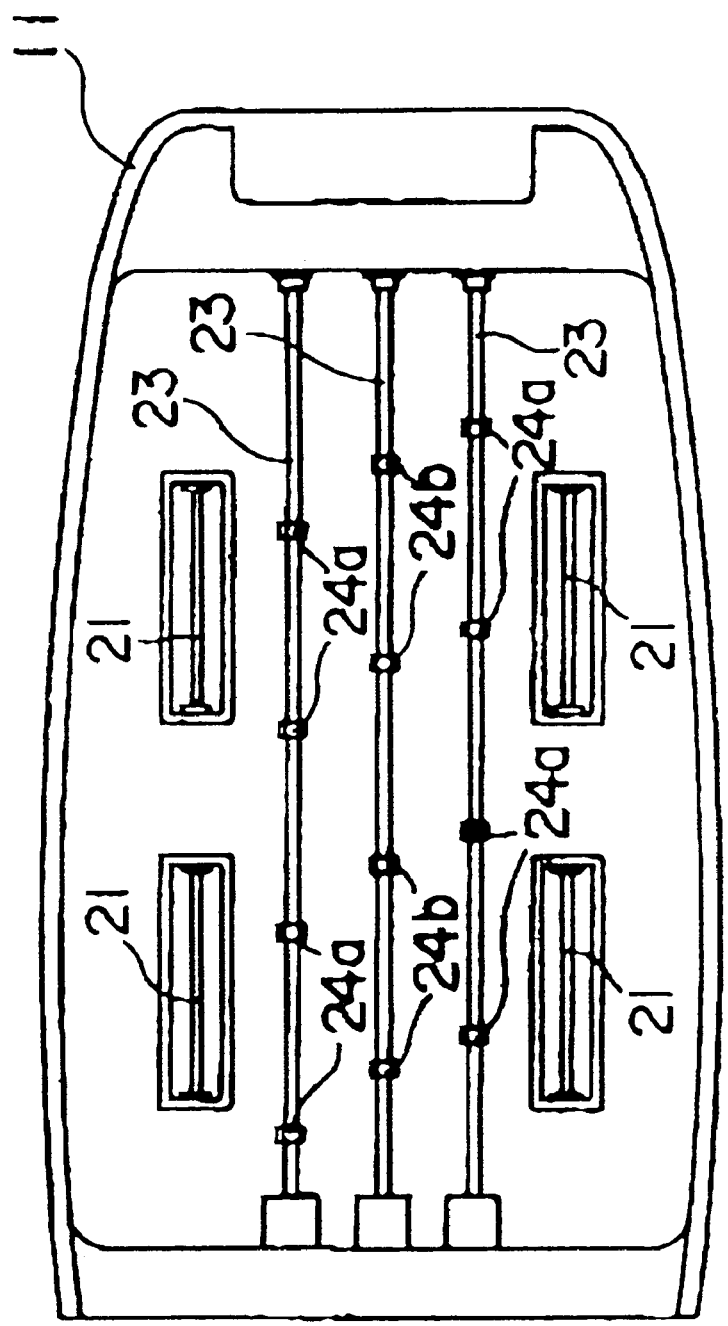
FIG. 8 is a bottom view of the lid 11, i.e., a view of its back side.

FIG. 7 is a block diagram showing the main electrical configuration of the bathing apparatus according to the present invention.

The bathing apparatus according to the present invention has a control unit 100 consisting of a CPU 101 to carry out logical calculations, a ROM 102 to store operating programs necessary to control the apparatus and a RAM 103 to temporarily store data or the like. This control unit 100 is connected via an interface 104 to an operation control unit 106 to control operation of the abovementioned sensors, pumps, valves and heaters. Further, the control unit 100 is connected via the interface 104 to an operation panel 105, which is mounted on the lid 11 (see FIG. 1), to input various data.

Next, bathing operation using the bathing apparatus having the abovementioned structure will be explained.

Prior to bathing, a prescription for bathing is input via the operation panel 105 by the subject to be bathed M or an operator. In this state, hot water at a specified temperature is filled into the hot-water storage tank 43 and steam is being generated from the aroma-containing hot water in the steam generation part 90.

Next, the lid 11 is opened as shown with the double-dotted broken line in FIG. 1. The subject to be bathed M then enters the main apparatus 10 and lies on the supporting member 13, after which the lid 11 is closed as shown with the solid line in FIG. 1. In this state, only the head of the subject to be bathed M is exposed to external air and its body remains inside of the main apparatus 10. Further, the waterproof curtain 17 is placed around the neck of the subject to be bathed M. In this state, there is a very little opening around the neck of the subject to be bathed M.

Bathing starts in this state. First, the shower pump 45 is operated while the solenoid valve 46 in the liquid supply system 41 remains open. Thereby, hot water is supplied from the hot-water storage tank 43 to the upper nozzles 24 and the lower nozzles 25, then ejected onto the subject to be bathed M.

At the same time, the motor 35 shown in FIG. 4 is driven to turn each shaft 23 so as to cause the upper nozzles 24 and the lower nozzles 25 to swing in the left-right direction relative to the subjects to be bathed M. Hot water is supplied over the entire body of the subject to be bathed M by this swinging. Thus, the swinging can also improve the showering effect with hot water supplied from the upper nozzles 24 and the lower nozzles 25.

In this state, the tube pump 62 is operated. Thereby, the body soap stored in the body soap reservoir 52 is supplied via the body-soap supply route 57 to the hot-water supply route 44. This body soap is then admixed with the hot water passing through the hot-water supply route 44. Thereby, the body soap is supplied, like a shower, to the entire body of the subject to be bathed M from the swinging upper nozzles 24 and lower nozzles 25 to cleanse the body of the subject to be bathed M.

Next, the operation of the tube pump 62 is stopped. Thereby, only hot water is supplied, like a shower, from the swinging upper nozzles 24 and lower nozzles 25, to the entire body of the subject to be bathed M. The body soap supplied to the subject to be bathed M is removed by this hot water shower.

The tube pump 64 is then operated. Thereby, the seaweed pack stored in the seaweed-pack reservoir 54 is supplied via the seaweed-pack supply route 59 to the hot-water supply route 44. Since the seaweed pack is water soluble, it can be readily mixed with hot water. This seaweed pack is then admixed with the hot water passing through the hot-water supply route 44. Thereby, the seaweed pack is supplied, like a shower, to the entire body of the subject to be bathed M from the swinging upper nozzles 24 and lower nozzles 25. This seaweed pack can make the skin of the subject to be bathed M healthy.

Next, the shower pump 45 and the tube pump 64 are stopped. Then, the ventilator 68 and the heater 69 are started to supply warm air from the warm air generation part 80 to the steam generation part 90. In the steam generation part 90, aroma-containing steam is admixed with the warm air generated in the warm air generation part 80. This aroma-containing steam is supplied, via the ventilation pipe 70, to the pair of warm air ejection parts 22 placed in the base 12, and filled into the main apparatus 10.

At the same time, a plurality of far-infrared emission lamps 21 placed in the back side of the lid 11 are lit.

Far-infrared rays from the far-infrared emission lamps 21 radiate the subject to be bathed M.

In this state, the body, to the inside, of the subject to be bathed M is warmed up from the inside and perspiration is enhanced by the warm air mixed with steam and far-infrared radiation. This promotes body metabolism to improve the effect of one's diet.

Further, the body of the subject to be bathed M can be warmed up only by hot water mixed with steam or by far-infrared radiation only.

In this connection, the aroma-containing steam filled into the main apparatus 10 is released outside through the narrow opening around the neck of the subject to be bathed M. Thereby, the subject to be bathed M can fully inhale the aroma-containing steam. As a result, the relaxation effect on the subject to be bathed M can be improved.

Next, warm air generation by the warm air generation part 80 is stopped and at the same time, the far-infrared emission lamps 21 are turned off. The shower pump 45 and the tube pump 64 are restarted to supply a seaweed pack, like a shower, onto the entire body of the subject to be bathed M.

Next, the tube pump 64 is stopped. Thereby, only hot water is supplied like a shower via the swinging upper nozzles 24 and lower nozzles 25 onto the entire body of the subject to be bathed M. By this hot water shower, the seaweed pack supplied on the subject to be bathed M is removed.

The tube pump 63 is then started. Thereby, lotion stored in the lotion reservoir 53 is supplied to the hot-water supply route 44 via the lotion supply route 58. This lotion is then admixed with hot water passing through the hot-water supply route 44. Thereby, the lotion is supplied, like a shower, via the swinging upper nozzles 24 and lower nozzles 25 onto the entire body of the subject to be bathed M. This lotion can maintain the skin of the subject to be bathed M in its optimal condition.

Thereafter, the shower pump 45 and the tube pump 64 are stopped. The ventilator 68 and the heater 69 are then started to restart warm air generation by the warm air generation part 80. Thereby, the body of subject to be bathed M is warmed up and drying of water drops on the body of the subject to be bathed M can be enhanced.

After completion of the procedure above, the lid 11 is moved to the open position, as shown with the double-dotted broken line in FIG. 1, to let out the subject to be bathed M.

The inside of the main apparatus 10 is washed after completion of the abovementioned bathing procedure. In washing the apparatus, the lid 11 is placed in the closed position as shown with the solid line in FIG. 1, after which the shower pump 45 and the tube pump 60 are started. Thereby, a cleansing agent stored in the cleansing agent reservoir 50 is supplied to the hot-water supply route 44 via the cleansing-agent supply route 55. This cleansing agent is then admixed with the hot water passing through the hot-water supply route 44.

In this state, the shafts 23 are turned 360 degrees by the motor 35 in FIG. 4. Thereby, a mixture of hot water ejected from the upper nozzles 24 and the lower nozzles 25 and the cleansing agent is supplied toward the entire inner wall of the lid 11 and the base 12. Thus, the main apparatus 10 can be entirely washed with the cleansing liquid.

Next, the tube pump 60 is stopped and the tube pump 61 is started. Thereby, a disinfectant stored in the disinfectant reservoir 51 is supplied via the disinfectant supply route 56 to the hot-water supply route 44. Thus, this disinfectant is admixed with hot water passing through the hot-water supply route 44.

Thereby, a mixture of the hot water and the disinfectant ejected via the upper nozzles 24 and the lower nozzles 25 is supplied onto the entire inner walls of the lid 11 and the base 12. Thus, the main apparatus 10 can entirely be disinfected with the disinfectant.

Further, in the abovementioned embodiment, the warm air mixed with stream is supplied to the main apparatus 10 by generating warm air in the warm air generation part 80, only in necessary steps. However, the warm air mixed with stream can be filled constantly into the main apparatus 10 by operating the warm air generation part 80 in every step.

The following is another embodiment according to the present invention. The description which is the same as in the aforesaid embodiment is omitted, and FIGS. 1, 2, 4, and 6–9 are applicable to this embodiment.

Three shafts 23 which can each turn around its axial center are located on the lid 11. Upper shower nozzles 24a are mounted on the shafts 23 located on both sides. Upper spray nozzles 24b are mounted on the shaft 23 located in the center.

Three shafts 23 which can each turn around its axial center are also located under the supporting member 13 in the base 12. Lower shower nozzles 25a are mounted on the shafts 23 located on both sides. Lower spray nozzles 25b are mounted on the shaft 23 located in the center.

The abovementioned upper shower nozzles 24a and lower shower nozzles 25a are to eject hot water or the like, described hereinafter, like a shower. Further, the abovementioned upper spray nozzles 24b and lower spray nozzles 25b are to eject lotion or a seaweed pack, described hereinafter, like a mist.

These shafts mounted with the upper shower nozzles 24a, the lower shower nozzles 25a, the upper spray nozzles 24b and the lower spray nozzles 25b each turn round its axial center by a shaft driving mechanism described hereinafter. The upper shower nozzles 24a, the lower shower nozzles 25a, the upper spray nozzles 24b and the lower spray nozzles 25b swing with the rotation of the shafts 23.

FIG. 4 is a cross section view of the shaft driving mechanism to turn these shafts 23. In FIG. 4, the upper shower nozzles 24a and the upper spray nozzles 24b are shown with symbol 24, and the lower shower nozzles 25a and the lower spray nozzles 25b are shown by symbol 25.

One end of the shaft 23 pivots via a bearing 31 on the side wall 32 of the lid 11 or base 12. An O-ring 33 is placed between the shaft 32 and the bearing 31 to form an airtight connection between the outer perimeter of the shaft 23 and the inner perimeter of the bearing 31. The other end of the shaft 23 is connected, via a coupling 34, to a motor 35 mounted on the main apparatus. Thereby, the shaft 23 turns synchronously with the upper shower nozzles 24a (or lower shower nozzles 25a, upper spray nozzles 24b, lower spray nozzles 25b) mounted on it.

These shafts 23 are set in the head-to-leg direction of of the subject to be bathed M (parallel with the supine subject to be bathed M). Accordingly, as the abovementioned shafts 23 turn, the upper shower nozzles 24a (or lower shower nozzles 25a, upper spray nozzles 24b, lower spray nozzles 25b) swing in a left-and-right motion (up-and-down direction in FIGS. 2 and 8).

As shown in FIG. 4, the abovementioned shafts 23 are cylindrical having one end plugged by a stopper 36. Of these shafts 23, the shafts 23 on both sides are connected to a hot-water supply route 44, described hereinafter, to supply hot water or the like to the upper shower nozzles 24a (or lower shower nozzles 25a). Thereby, hot water or the like supplied from the hot-water supply route 44 runs through the shafts 23 and is ejected like a shower from the upper shower nozzles 24a (or lower shower nozzles 25a) toward the subject to be bathed M. Thus, the hot water or the like is supplied on the entire body of the subject to be bathed M with the swinging motion of the upper shower nozzles 24a (or lower shower nozzles 25a).

Similarly, of these shafts 23, the shafts 23 in the center is connected to a lotion supply route 55 to supply lotion or a seaweed-pack supply route 56 to supply a seaweed pack, to the upper spray nozzles 24b (or lower spray nozzles 25a). Thereby, the lotion or the seaweed pack supplied from the lotion supply route 55 or the seaweed supply route 56 runs through the shafts 23 and is ejected like a mist from the upper spray nozzles 24b (or lower spray nozzles 25b) toward the subject to be bathed M. Thus, the lotion of the seaweed pack is supplied to the entire body of the subject to be bathed M with the swinging motion of the upper spray nozzles 24b (or lower spray nozzles 25b).

Figure 9:
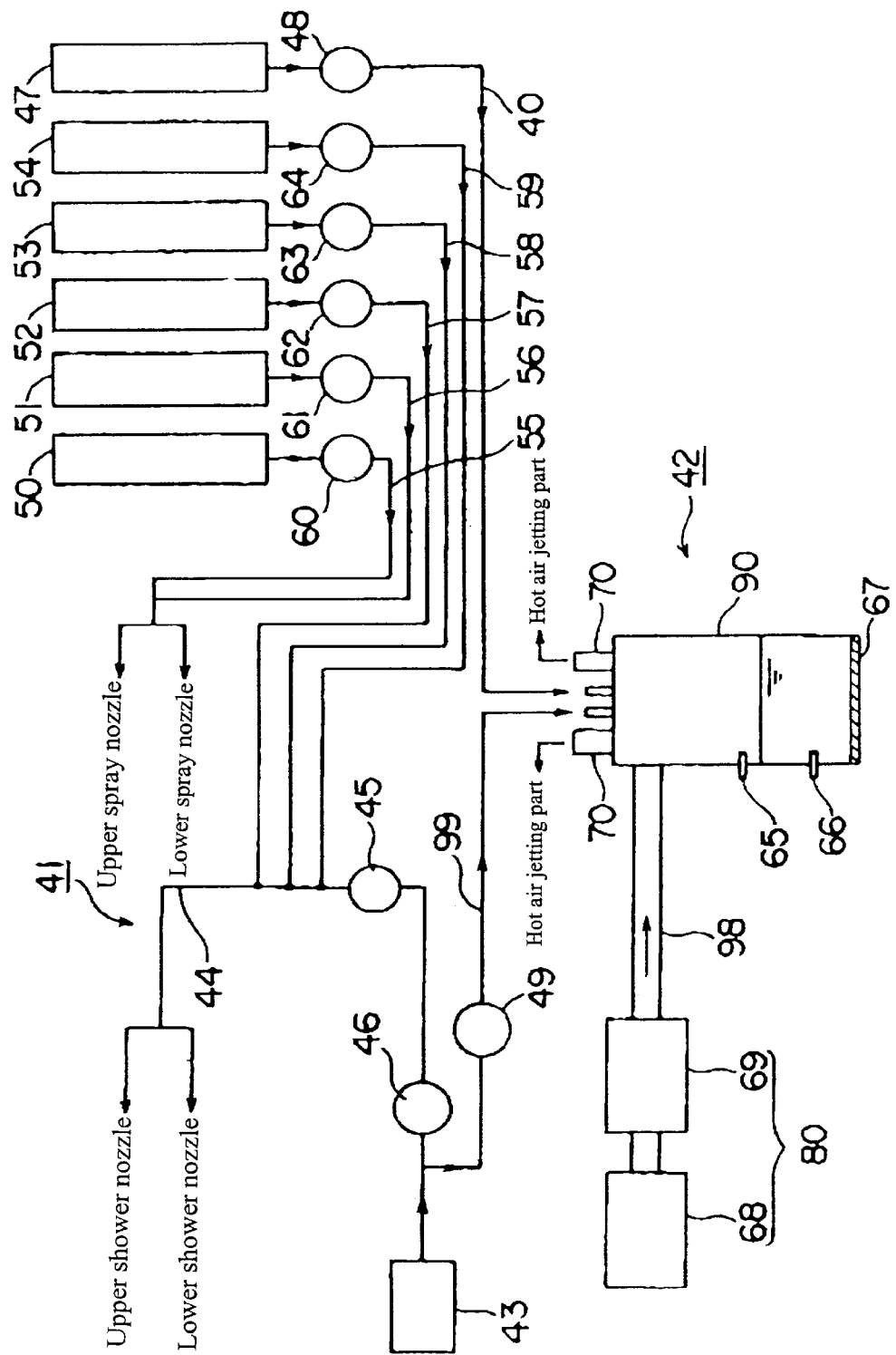
FIG. 9 is a block diagram showing the liquid supply system 41 and the steam/warm air supply system 42.

Next, the structures of the liquid supply system 41 to supply hot water or the like to the abovementioned upper shower nozzles 24a and lower shower nozzles 25a and to supply lotion and a seaweed pack to the upper spray nozzles 24a and the lower spray nozzles 25b and a steam/warm-air supply system 42 to supply warm air mixed with steam to warm-air ejection parts 22 will be explained. FIG. 9 is a block diagram of the liquid supply system 41 and the steam/warm-air supply system 42.

The liquid supply system 41 has a hot-water supply route 44 to supply hot water stored in a hot-water storage tank 43, described in detail hereinafter, to the upper shower nozzles 24a and the lower shower nozzles 25a. A solenoid valve 46 and a shower pump 45 are placed in this hot-water supply route 44. By operating the shower pump 45 while the solenoid valve 46 is opened, hot water stored in the hot-water storage tank 43 is moved to the upper shower nozzles 24a and the lower shower nozzles 25a and ejected from these upper shower nozzles 24a and lower shower nozzles 25a onto the subject to be bathed M in the main apparatus 10.

Further, the liquid supply system 41 has a cleansing agent reservoir 53 to store a cleansing agent to clean inside the main apparatus 10, a disinfectant reservoir 54 to store a disinfectant to disinfect inside the main apparatus 10, a body soap reservoir 52 to store a body soap to wash human bodies, a lotion reservoir 50 to store lotion and a seaweed-pack reservoir 51 to store a seaweed pack as a water-soluble pack.

The abovementioned cleansing agent reservoir 53 is connected to the hot-water supply route 44 via a cleansing-agent supply route 58. A tube pump 63 to move a small amount of cleansing agent is placed inside the cleansing-agent supply route 58. Thus, by operating the tube pump 63, the cleansing agent stored in the cleansing agent reservoir 53 is moved toward the hot-water supply route 44 and a desired amount of the cleansing agent is mixed with hot water and thus can be supplied to the upper shower nozzles 24a and the lower shower nozzles 25a.

Similarly, the abovementioned disinfectant reservoir 54 is connected to the hotwater supply route 44 via a disinfectant supply route 59. A tube pump 64 to move a small amount of cleansing agent is placed inside the disinfectant supply route 59. Thus, by operating the tube pump 64, the disinfectant stored in the disinfectant reservoir 54 is moved toward the hot-water supply route 44 and a desired amount of the disinfectant is mixed with hot water and thus can be supplied to the upper shower nozzles 24a and the lower shower nozzles 25a.

Similarly, the abovementioned body soap reservoir 52 is connected to the hot-water supply route 44 via a body soap supply route 57. A tube pump 62 to move a small amount of body soap is placed inside the body soap supply route 57. Thus, by operating the tube pump 62, the body soap stored in the body soap reservoir 52 is moved toward the hot-water supply route 44 and a desired amount of the body soap is mixed with hot water and thus can be supplied to the upper shower nozzles 24a and the lower shower nozzles 25a.

The abovementioned lotion reservoir 50 is connected to the upper spray nozzles 24b and the lower spray nozzles 25b via a lotion supply route 55. A tube pump 60 to move a small amount of lotion is placed inside the lotion supply route 58. Thus, by operating the tube pump 60, the lotion stored in the lotion reservoir 50 is moved toward the upper spray nozzles 24b and the lower spray nozzles 25b and a desired amount of the lotion can be ejected from the upper spray nozzles 24b and the lower spray nozzles 25b.

Similarly, the abovementioned seaweed-pack reservoir 51 is connected to the upper spray nozzles 24b and the lower spray nozzles 25b via a seaweed-pack supply route 56. A tube pump 61 to move a small amount of seaweed pack is placed inside the seaweed-pack supply route 56. Thus, by operating the tube pump 61, the seaweed pack stored in the seaweed-pack reservoir 51 is moved toward the upper spray nozzles 24b and the lower spray nozzles 25b and a desired amount of the seaweed pack can be ejected from the upper spray nozzles 24b and the lower spray nozzles 25b.

As explained previously, prior to bathing, a prescription for bathing is input via the operation panel 105 by the subject to be bathed M or an operator. In this state, hot water at a specified temperature is filled into the hot-water storage tank 43 and steam is being generated from the aroma-containing hot water in the steam generation part 90. Next, the lid 11 is opened as shown with the double-dotted broken line in FIG. 1. The subject to be bathed M then enters the main apparatus 10 and lies on the supporting member 13, after which the lid 11 is closed as shown with the solid line in FIG. 1. In this state, only the head of the subject to be bathed M is exposed to external air and its body remains inside of the main apparatus 10. Further, the waterproof curtain 17 is placed around the neck of the subject to be bathed M. In this state, there is a very little opening around the neck of the subject to be bathed M.

Bathing starts in this state. First, the shower pump 45 is operated while the solenoid valve 41 in the liquid supply system 41 remains open. Thereby, hot water is supplied from the hot-water storage tank 43 to the upper shower nozzles 24a and the lower shower nozzles 25a, then ejected onto the subject to be bathed M.

At the same time, the motor 35 shown in FIG. 4 is driven to turn each shaft 23 so as to cause the upper shower nozzles 24a and the lower shower nozzles 25a to swing in the left-right direction relative to the subject to be bathed M. Hot water is supplied onto the entire body of the subject to be bathed M by this swinging. Thus, the swinging can also improve the showering effect with hot water supplied from the upper shower nozzles 24a and the lower shower nozzles 25a.

At the same time, the tube pump 62 is operated. Thereby, the body soap stored in the body soap reservoir 52 is supplied via the body soap supply route 57 to the hot-water supply route 44. This body soap is then mixed with the hot water passing through the hot-water supply route 44. Thereby, the body soap is supplied, like a shower, to the entire body of the subject to be bathed M from the swinging upper shower nozzles 24a and the lower shower nozzles 25a to cleanse the body of the subject to be bathed M.

Next, the shower pump 62 is stopped. Thereby, only hot water is supplied, like a shower, from the swinging upper shower nozzles 24a and the lower shower nozzles 25a to the entire body of the subject to be bathed M. The body soap supplied to the subject to be bathed M is removed by this hot water shower.

Then, the shower pump 45 is stopped and at the same time, the tube pump 61 is operated. Thereby, the seaweed pack stored in the seaweed reservoir 51 is supplied via the seaweed supply route 56 to the upper spray nozzles 24b and the lower spray nozzles 25b. Thereby, the seaweed pack is supplied like a mist to the entire body of the subject to be bathed M from the swinging upper shower nozzles 24a and the lower shower nozzles 25a. This seaweed pack can make the skin of the subject to be bathed M healthy.

Next, the tube pump 61 is stopped. Then, the ventilator 68 and the heater 69 are started to supply warm air from the warm-air generation part 80 to the steam generation part 90. In the steam generation part 90, aroma-containing steam is mixed with the warm air generated in the warm-air generation part 80. This aroma-containing steam is supplied, via the ventilation pipe 70, to the pair of the warm-air ejection parts 22 placed in the base 12, and filled into the main apparatus 10.

At the same time, a plurality of far-infrared emission lamps 21 placed in the back side of the lid 11 are lit. Far-infrared rays from the far-infrared emission lamps 21 radiate the subject to be bathed M.

In this state, the body of the subject to be bathed M is warmed up from the inside and perspiration is enhanced by the warm air mixed with steam and far-infrared radiation. This promotes body metabolism to improve the effect of one's diet.

Further, the body of the subject to be bathed M can be warmed up only by hot water mixed with steam or by far-infrared radiation only.

In this connection, the aroma-containing steam filled into the main apparatus 10 is released outside through the narrow opening around the neck of the subject to be bathed M. Thereby, the subject to be bathed M can fully inhale the aroma-containing steam. As a result, the relaxation effect on the subject to be bathed M can be improved.

Next, warm air generation by the warm-air generation part 80 is stopped and at the same time, the far-infrared emission lamps 21 are turned off. The tube pump 61 is restarted to supply a seaweed pack, like a mist, onto the entire body of the subject to be bathed M.

Next, the tube pump 61 is stopped and at the same time, the shower pump 45 is started. Thereby, only warm water is supplied like a shower from the upper shower nozzles 24a and the lower shower nozzles 25a. By this hot water shower, the seaweed pack supplied on the subject to be bathed M is removed.

Then, the shower pump 45 is stopped and at the same time, the tube pump 60 is started. Thereby, lotion stored in the lotion reservoir 50 is supplied to the upper spray nozzles 24b and the lower spray nozzles 25b via the lotion supply route 55. Thereby, the lotion is supplied, like a mist, via the swinging upper spray nozzles 24b and the lower spray nozzles 25b onto the entire body of the subject to be bathed M. This lotion can maintain the skin of the subject to be bathed M in its optimal condition.

Thereafter, the tube pump 61 is stopped. The ventilator 68 and the heater 69 are then started to restart warm air generation by the warm-air generation part 80. Thereby, the body of subject to be bathed M is warmed up and the drying of water drops adhering on the body of the subject to be bathed M can be enhanced. In this moment, the far-infrared emission lamps 21 can be lit.

After completion of the procedure above, the lid 11 is moved to the open position, as shown with the double-dotted broken line in FIG. 1, to let out the subject to be bathed M.

The inside of the main apparatus 10 is washed after completion of the abovementioned bathing procedure. In washing the apparatus, the lid 11 is placed in the closed position as shown by the solid line in FIG. 1, after which the shower pump 45 and the tube pump 63 are started. Thereby, a cleansing agent stored in the cleansing agent reservoir 53 is supplied to the hot-water supply route 44 via the cleansing-agent supply route 55. This cleansing agent is then mixed with the hot water passing through the hot-water supply route 44.

In this state, the shafts 23 are turned 360 degrees by the motor 35 in FIG. 4. Thereby, a mixture of hot water ejected from the upper shower nozzles 24a and the lower shower nozzles 25a and the cleansing agent is supplied toward the entire inner wall of the lid 11 and the base 12. Thus, the main apparatus 10 can entirely be washed with the cleansing liquid.

Next, the tube pump 63 is stopped and the tube pump 64 is started. Thereby, a disinfectant stored in the disinfectant reservoir 54 is supplied via the disinfectant supply route 59 to the hot-water supply route 44. Thus, this disinfectant is mixed with hot water passing through the hot-water supply route 44.

Thereby, a mixture of hot water and the disinfectant ejected via the upper shower nozzles 24a and the lower shower nozzles 25a is supplied towards the entire inner wall of the lid 11 and the base 12. Thus, the main apparatus 10 can entirely be disinfected with the disinfectant.

Further, in the abovementioned embodiment, the warm air mixed with stream is supplied to the main apparatus 10 by generating warm air in the warm air generation part 80, only in necessary steps. However, the warm air mixed with stream can be filled constantly into the main apparatus 10 by operating the warm air generation part 80 in every step.

[Effectiveness of the Invention]

According to the invention as claimed in claim 1, a subject to be bathed M can enjoy not only an effective cleasning but also a cosmetic treatment and a health effect by relaxation or the like. Thereby, the beauty and health of the subject to be bathed M can be improved.

According to the invention as claimed in claim 2, far-infrared radiation can warm up a human body and enhance perspiration since the heating means includes a far-infrared emission system to radiate far-infrared rays onto the space formed by the base and the lid.

According to the invention as claimed in claim 3, warm air can warm up a human body and enhance perspiration since the heating means includes a warm-air supply system.

According to the invention as claimed in claim 4, an appropriate amount of steam can be effectively supplied to a space formed by the base and the lid since a steam supply system to mix steam with warm air passing through a warm-air supply route is further included, although its configuration is simple.

According to the invention as claimed in claim 5, a human body can be bathed more effectively since the apparatus further comprises a cleansing agent reservoir to store a cleansing agent to wash the human body and a cleansing agent supply means to mix the cleansing agent, stored in the cleansing agent reservoir, with hot water passing through the hot-water supply route. In this connection, the cleansing agent can be effectively supplied to the human body since the cleansing agent is added into the warm water, although its configuration is simple.

According to the invention as claimed in claim 6, skin of the human body can be maintained in the optimal condition since the apparatus further comprises a lotion reservoir to store lotion, spray nozzles to eject the lotion stored in the lotion reservoir like a mist into a space formed by the base and the lid and a lotion supply route to connect the spray nozzles and the lotion reservoir. In this connection, the expensive lotion can be effectively applied to the human body without loss since the lotion can be supplied like a mist.

According to the invention as claimed in claim 7, skin of the human body can be conditioned into a healthy state since the apparatus further comprises a water-soluble pack reservoir to store a water-soluble pack and a water-soluble pack supply route to connect the spray nozzles and the water-soluble pack reservoir. In this connection, expensive water-soluble pack can be effectively supplied to the human body without loss since the water-soluble pack can be applied like a mist.

According to the invention as claimed in claim 8, lotion or a water-soluble pack can be supplied to both the front and back side of the human body since the spray nozzles comprise a plurality of upper spray nozzles placed on the lid and a plurality of lower spray nozzles placed under the body supporting member in the base.

According to the invention as claimed in claim 9, hot water or the like can be effectively supplied onto the entire human body and the cleansing effect can be improved since the apparatus further comprises a swinging means to swing the upper shower nozzles and the lower shower nozzles.

According to the invention as claimed in claim 10, lotion or the water-soluble pack can be effectively supplied onto the entire human body since the apparatus further comprises the swinging means to swing spray nozzles.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A bathing apparatus comprising:
    a base having an opening on the top;
    a body supporting member having a number of openings, placed in said base;
    a lid covering the opening of said base;
    a plurality of upper shower nozzles arranged on said lid;
    a plurality of lower shower nozzles arranged under the body supporting member in said base;
    a hot-water supplying part;
    a hot-water supply route to connect a plurality of said upper shower nozzles and a plurality of said lower shower nozzles and said hot-water supplying part, said hot-water supplying route including: (i) at least one upper hollow shaft extending from one side to another side of the lid substantially in parallel to the body supporting member, each upper shaft having two ends rotatably fixed to the lid, wherein the upper shower nozzles are mounted on each upper shaft; and (ii) at least one lower hollow shaft extending from one side to another side of the base substantially in parallel to the body supporting member, each lower shaft having two ends rotatably fixed to the base, wherein the lower shower nozzles are mounted on each lower shaft, wherein hot water flows inside each upper and lower shaft;
    an actuator to partially rotate each of said upper and lower hollow shafts on its axis; and
    a heater to heat a space formed by said base and said lid.

2. A bathing apparatus as claimed in claim 1, wherein said heater includes a far-infrared emission system to radiate far-infrared rays onto a space formed by said base and said lid.

3. A bathing apparatus as claimed in claim 1, wherein said heater includes a warm-air supply system having a warm-air generation part, a warm-air ejection part and a warm-air supply route to connect said warm-air ejection part and said warm-air generation part.

4. A bathing apparatus as claimed in claim 1, further comprising
    a cleansing agent reservoir to store a cleansing agent to cleanse a human body, and
    a mixer to mix the cleansing agent, stored in said cleansing agent reservoir, with hot water passing through said hot-water supply route.

5. A bathing apparatus as claimed in claim 4 further comprising
    a lotion reservoir to store lotion,
    spray nozzles to eject like a mist the lotion stored in said lotion reservoir onto a space formed by said base and said lid, and
    a lotion supply route to connect said spray nozzles and said lotion reservoir.

6. A bathing apparatus as claimed in claim 5 further comprising
    a water-soluble-pack reservoir to store a water-soluble pack,
    spray nozzles to eject, like a mist, the water-soluble pack stored in said water-soluble-pack reservoir onto a space formed by said base and said lid, and
    a water-soluble-pack supply route to connect said spray nozzles and said water-soluble-pack reservoir.

7. A bathing apparatus as claimed in claim 6, wherein said lotion supply route includes (i) at least one hollow shaft extending from one side to another side of at least either the lid or the base substantially in parallel to the body supporting member, said shaft having two ends rotatably fixed to the lid or the base, wherein the spray nozzles are mounted on said shaft, wherein the lotion flows inside the shaft, and (ii) an actuator to swing the shaft on its axis.

8. A bathing apparatus as claimed in claim 7, wherein the shaft of the pack supply route is aligned with the shaft of the hot-water supply route.

9. A bathing apparatus as claimed in claim 5, wherein said spray nozzles comprise a plurality of upper spray nozzles arranged on said lid and a plurality of lower spray nozzles arranged under the body supporting member in said base.

10. A bathing apparatus as claimed in claim 5, wherein said lotion supply route includes (i) at least one hollow shaft extending from one side to another side of at least either the lid or the base substantially in parallel to the body supporting member, said shaft having two ends rotatably fixed to the lid or the base, wherein the spray nozzles are mounted on said shaft, wherein the lotion flows inside the shaft, and (ii) an actuator to swing the shaft on its axis.

11. A bathing apparatus as claimed in claim 9, wherein the shaft of the lotion supply route is aligned with the shaft of the hot-water supply route.

12. A bathing apparatus as claimed in claim 1 further comprising a swinging device to swing said upper and lower shower nozzles.

13. A bathing apparatus comprising:

a base having an opening on the top;

a body supporting member having a number of openings, placed in said base;

a lid covering the opening of said base;

a plurality of upper shower nozzles arranged on said lid;

a plurality of lower shower nozzles arranged under the body supporting member in said base;

a hot-water supplying part;

a hot-water supply route to connect a plurality of said upper shower nozzles and a plurality of said lower shower nozzles and said hot-water supplying part; and a heater to heat a space formed by said base and said lid, wherein said heater includes a warm-air supply system having a warm-air generation part, a warm-air ejection part and a warm-air supply route to connect said warm-air ejection part and said warm-air generation part, said bathing apparatus further comprising a steam supply system to mix steam with warm air passing through said warm-air supply route.

14. A bathing apparatus comprising a main apparatus comprising of a base having an opening on the top and a body supporting member inside and a lid covering the opening of the base;

a hot water supplyer to supply hot water to a human body in said main apparatus;

a cleansing agent supplyer to supply a cleansing agent to a human body in said main apparatus; and a far-infrared supplyer to radiate far-infrared rays onto a human body in said main apparatus, wherein said main apparatus includes (i) at least one hollow shaft extending from one side to another side of the main apparatus substantially in parallel to the body supporting member, each shaft having shower nozzles mounted thereon and having two ends rotatably fixed to the main apparatus, wherein each shaft connects to the hot water supplyer, and hot water flows inside the shaft and is ejected through the nozzles; and (ii) an actuator to partially rotate each shaft on its axis.

15. A bathing apparatus as claimed in claim 14 further comprising a lotion supplyer to supply lotion to a human body in said main apparatus.

16. A bathing apparatus as claimed in claim 15 further comprising a water-soluble-pack supplyer to supply a water-soluble pack to a human body in said main apparatus.

17. A bathing apparatus comprising a main apparatus comprising of a base having an opening on the top and a body supporting member inside and a lid covering the opening of the base;

a hot water supplyer to supply hot water to a human body in said main apparatus;

a cleansing agent supplyer to supply a cleansing agent to a human body in said main apparatus; and a far-infrared supplyer to radiate far-infrared rays onto a human body in said main apparatus, said bathing apparatus further comprising a steam mixer to admix steam with warm air supplied by a warm air supplyer.

* * * * *